US011510858B2

(12) United States Patent
King et al.

(10) Patent No.: US 11,510,858 B2
(45) Date of Patent: Nov. 29, 2022

(54) CLEANSING COMPOSITION

(71) Applicant: GlaxoSmithKline Consumer Healthcare (UK) IP Limited, Brentford (GB)

(72) Inventors: Simon King, Weybridge (GB); Alexander Thomas Platts, Weybridge (GB)

(73) Assignee: GLAXOSMITHKLINE CONSUMER HEALTHCARE (UK) IP LIMITED, Brentford Middlesex (GB)

(*) Notice: Subject to any disclaimer, the term of this patent is extended or adjusted under 35 U.S.C. 154(b) by 74 days.

(21) Appl. No.: 16/466,430

(22) PCT Filed: Dec. 4, 2017

(86) PCT No.: PCT/EP2017/081299
§ 371 (c)(1),
(2) Date: Jun. 4, 2019

(87) PCT Pub. No.: WO2018/104200
PCT Pub. Date: Jun. 14, 2018

(65) Prior Publication Data
US 2020/0060954 A1 Feb. 27, 2020

(30) Foreign Application Priority Data

Dec. 6, 2016 (GB) ...................... 1620701

(51) Int. Cl.
*A61K 8/49* (2006.01)
*A61K 8/34* (2006.01)
*A61K 8/02* (2006.01)
*A61Q 11/02* (2006.01)

(52) U.S. Cl.
CPC .......... *A61K 8/4993* (2013.01); *A61K 8/0208* (2013.01); *A61K 8/34* (2013.01); *A61Q 11/02* (2013.01); *A61K 2800/30* (2013.01)

(58) Field of Classification Search
CPC ......... A61K 8/4993; A61K 8/34; A61Q 11/02
See application file for complete search history.

(56) References Cited

U.S. PATENT DOCUMENTS

| 8,551,508 B2* | 10/2013 | Lee .......... C03C 3/115 424/401 |
| 8,632,636 B1* | 1/2014 | Tricca .......... C11D 7/261 134/6 |
| 2006/0204453 A1* | 9/2006 | Giniger .......... A61K 8/90 424/49 |
| 2010/0119461 A1* | 5/2010 | Bicard-Benhamou .......... A61Q 19/008 424/59 |
| 2013/0017239 A1* | 1/2013 | Viladot Petit .......... A61Q 3/00 424/401 |
| 2013/0189196 A1* | 7/2013 | Tamarkin .......... A61K 8/8152 424/47 |
| 2013/0216596 A1* | 8/2013 | Viladot Petit .......... A61K 8/64 424/463 |
| 2018/0140084 A1* | 5/2018 | Blachford .......... A61C 17/036 |
| 2020/0060954 A1* | 2/2020 | King .......... A61K 8/4973 |

FOREIGN PATENT DOCUMENTS

| EA | 13501 B1 | 6/2010 | |
| FR | 2649318 | 1/1991 | |
| FR | 2649318 A1 * | 1/1991 | ............ A61K 9/70 |
| GB | 901554 A | 7/1962 | |
| JP | H01-238517 A | 9/1989 | |
| JP | H11-197164 A | 7/1999 | |
| JP | 2002-540134 A | 11/2002 | |
| JP | 2010-006720 A | 1/2010 | |
| JP | 2010-018544 A | 1/2010 | |
| JP | 2010-168352 A | 8/2010 | |
| RU | 2572882 C2 | 1/2016 | |
| WO | WO 9913717 | 3/1999 | |
| WO | 2000057849 A1 | 10/2000 | |
| WO | WO 2006/113227 | 10/2006 | |
| WO | WO-2006113227 A2 * | 10/2006 | ........... A61K 8/0208 |
| WO | WO-2007147815 A1 * | 12/2007 | ............ A61K 8/22 |
| WO | 2010084480 A2 | 7/2010 | |

OTHER PUBLICATIONS

Kiesow Andreas et al: "Material compatibility and antimicrobial activity of consumer products commonly used to clean dentures", Journal of Prosthetic Dentistry, Elsevier, Amsterdam, NL, vol. 115, No. 2, Nov. 3, 2015 (Nov. 3, 2015), p. 189, XP029398116, ISSN: 0022-3913, DOI: 10.1016/J.PROSDENT.2015.08.010 cited in the application abstract.

Axe, As, et al., Journal of Prosthetic Dentistry, Feb. 2016, vol. 115(2), 183-8.

* cited by examiner

*Primary Examiner* — Liam J Heincer
*Assistant Examiner* — M. Reza Asdjodi
(74) *Attorney, Agent, or Firm* — Roshni A. Sitapara

(57) ABSTRACT

Dental appliance cleansing composition comprising (a) fatty acid isopropyl ester, (b) polyoxyethylene sorbitan ester, (c) second sorbitan ester, wherein the cleansing composition does not contain methanol, ethanol or isopropyl alcohol. Dental appliance cleansing wipe impregnated with the composition. Use of the dental appliance cleansing composition or wipe for cleaning dental appliances and dentures.

9 Claims, No Drawings

CLEANSING COMPOSITION

This application is a 371 of International Application No. PCT/EP2017/081299, filed Dec. 4, 2017, which claims the priority of GB Application No. GB 1620701.1 filed Dec. 6, 2016, which is incorporated herein in its entirety.

FIELD OF THE INVENTION

The present invention relates to a new dental appliance cleansing composition, particularly an alcohol-free composition. The present invention also relates to a dental appliance wipe impregnated with a cleansing composition and the use thereof in cleaning removable dental appliances.

BACKGROUND TO THE INVENTION

Many wearers of removable dental appliances report frequent throughout-the-day cleaning. Cleaning is particularly prevalent post-eating where wearers often experience food particles getting stuck under the dental appliance, which can be irritating and uncomfortable. To remove food particles, wearers generally either use a toothbrush or rinse the dental appliance with water. Both approaches have the disadvantage of requiring water and may require removal of the dental appliance, which is inconvenient when away from the home. In addition, repeated brushing of dentures with toothpaste has been found to cause scratching of denture acrylic (Kiesow et al., Journal of Prosthetic Dentistry, 2016, Vol. 115, No. 2, pp 189-198).

It is known that denture wearers use a variety of cleansing methods, including the use of mouthwash, which typically contains alcohol (ethanol) (Axe A S et al., Journal of Prosthetic Dentistry. 2016 February; 115(2):183-8). However, the use of both alcohol containing mouthwash and isopropyl alcohol (IPA) was found to cause damage to denture materials (Kiesow et al., Journal of Prosthetic Dentistry, 2016, Vol. 115, No. 2, pp 189-198). Furthermore, the use of alcohols may also be undesirable for some wearers of dental appliances, for example for cultural or religious reasons, while compositions containing alcohol may be undesirable for children wearing orthodontic retainers for example.

There is therefore a need for an alternative cleansing method which does not require water or rinsing, which does not damage the denture material, and which can be used discretely when away from the home. Alcohol-free cleansing compositions are also desirable because Kiesow et al showed that alcohol causes damage to polymethyl methacrylate (PMMA) components of denture.

U.S. Pat. No. 8,632,636 B1 discloses a wet wiper for cleaning removable dental appliances, which wet wiper comprises a water insoluble substrate; and a physiologically acceptable cleansing composition comprising ethyl alcohol.

SUMMARY OF THE INVENTION

In one aspect, the present invention provides a dental appliance cleansing composition comprising:
a) a fatty acid isopropyl ester;
b) a polyoxyethylene sorbitan ester; and
c) a second sorbitan ester;
wherein the cleansing composition does not contain methanol, ethanol or isopropyl alcohol.

In another aspect, the present invention provides a dental appliance cleansing composition comprising:
a) a fatty acid isopropyl ester;
b) a polyoxyethylene sorbitan ester; and
c) a second sorbitan ester;
wherein the cleansing composition does not contain alcohol.

In another aspect, the present invention provides a dental appliance wipe impregnated with a cleansing composition comprising:
a) a fatty acid isopropyl ester;
b) a polyoxyethylene sorbitan ester; and
c) a second sorbitan ester;
wherein the cleansing composition does not contain methanol, ethanol or isopropyl alcohol.

In another aspect, the present invention provides a dental appliance wipe impregnated with a cleansing composition comprising:
a) a fatty acid isopropyl ester;
b) a polyoxyethylene sorbitan ester; and
c) a second sorbitan ester;
wherein the cleansing composition does not contain alcohol.

In another aspect, the present invention provides the use of a dental appliance cleansing composition as defined above, or a dental appliance wipe as defined above, for cleaning dental appliances.

DETAILED DESCRIPTION OF THE INVENTION

The composition of the present invention has been found to provide good cleansing of dental appliances and significant removal of microorganisms, while minimising damage to the dental appliance material.

The composition of the present invention comprises an isotropic microemulsion chassis with high solvating capability, which is readily dispersible in water and contains orally acceptable, cost effective and easily sourced materials. Microemulsions display ultra-low interfacial tension properties and have a large interfacial area which makes them useful in cleaning and microbial removal.

In particular, the present invention provides a dental appliance cleansing composition comprising:
a) a fatty acid isopropyl ester;
b) a polyoxyethylene sorbitan ester; and
c) a second sorbitan ester;
wherein the cleansing composition does not contain methanol, ethanol or isopropyl alcohol.

In another aspect, the present invention provides a dental appliance cleansing composition comprising:
a) a fatty acid isopropyl ester;
b) a polyoxyethylene sorbitan ester; and
c) a second sorbitan ester;
wherein the cleansing composition does not contain alcohol.

In one aspect, the invention provides a dental appliance cleansing composition comprising:
a) a fatty acid isopropyl ester;
b) a polyoxyethylene sorbitan ester;
c) a second sorbitan ester; and
d) a solvent selected from propylene glycol, water, and a mixture thereof;
wherein the cleansing composition does not contain methanol, ethanol or isopropyl alcohol.

In one aspect, the invention provides a dental appliance cleansing composition comprising:
a) a fatty acid isopropyl ester selected from isopropyl palmitate, isopropyl myristate, and combinations thereof;
b) a polyoxyethylene sorbitan ester selected from polysorbate 60 (TWEEN 60), polysorbate 65 (TWEEN 65), polysorbate 80 (also known as polyoxyethylene (20) sorbitan monooleate or TWEEN 80), polysorbate 81 (TWEEN 81), polysorbate 85 (TWEEN 85), and combinations thereof; and c) a second sorbitan ester selected from sorbitan monostearate (also known as sorbitan stearate or SPAN 60), sorbitan monolaurate (SPAN 20), sorbitan palmitate (SPAN 40), and combinations thereof;

wherein the cleansing composition does not contain methanol, ethanol or isopropyl alcohol.

In one aspect, the invention provides a dental appliance cleansing composition comprising:

a) a fatty acid isopropyl ester selected from isopropyl palmitate, isopropyl myristate, and combinations thereof;

b) a polyoxyethylene sorbitan ester selected from polysorbate 60 (TWEEN 60), polysorbate 65 (TWEEN 65), polysorbate 80 (also known as polyoxyethylene (20) sorbitan monooleate or TWEEN 80), polysorbate 81 (TWEEN 81), polysorbate 85 (TWEEN 85), and combinations thereof;

c) a second sorbitan ester selected from sorbitan monostearate (also known as sorbitan stearate or SPAN 60), sorbitan monolaurate (SPAN 20), sorbitan palmitate (SPAN 40), and combinations thereof; and d) a solvent selected from propylene glycol, water, and a mixture thereof;

wherein the cleansing composition does not contain methanol, ethanol or isopropyl alcohol.

In one aspect, the present invention provides a dental appliance cleansing composition comprising a) isopropyl myristate;

b) polysorbate 80; and c) sorbitan laurate;

wherein the cleansing composition does not contain methanol, ethanol or isopropyl alcohol.

In one aspect, the invention provides a novel dental appliance cleansing composition comprising:

a) isopropyl myristate;

b) polysorbate 80;

c) sorbitan laurate; and d) a solvent selected from propylene glycol, water, and a mixture thereof;

wherein the cleansing composition does not contain methanol, ethanol or isopropyl alcohol.

In one aspect, the present invention provides a novel dental appliance cleansing composition as defined in any previous aspect, wherein the cleansing composition does not contain alcohol e.g. is alcohol free.

In one aspect, the present invention provides a dental appliance cleansing composition as defined in any previous aspect wherein the fatty acid isopropyl ester is present in an amount from 2 to 70% w/w, preferably from 5 to 65% w/w. In one aspect, when the dental appliance cleansing composition does not contain water as a solvent, the fatty acid isopropyl ester is present in an amount from 10 to 65% w/w. In another aspect, when the dental appliance cleansing composition contains water as a solvent, the fatty acid isopropyl ester is present in an amount from 3 to 15% w/w, preferably from 5 to 7% w/w.

In one aspect, the present invention provides a dental appliance cleansing composition as defined in any previous aspect wherein the polyoxyethylene sorbitan ester is present in an amount from 0.5 to 45% w/w, preferably from 0.7 to 40% w/w. In one aspect, when the dental appliance cleansing composition does not contain water as a solvent, the polyoxyethylene sorbitan ester is present in an amount from 10 to 45% w/w, preferably from 12 to 40% w/w. In another aspect, when the dental appliance cleansing composition contains water as a solvent, the polyoxyethylene sorbitan ester is present in an amount from 0.5 to 4% w/w, preferably from 1 to 2% w/w.

In one aspect, the present invention provides a dental appliance cleansing composition as defined in any previous aspect wherein the second sorbitan ester is present in an amount from 0.5 to 65% w/w, preferably from 0.7 to 60% w/w. In one aspect, when the dental appliance cleansing composition does not contain water as a solvent, the second sorbitan ester is present in an amount from 10 to 65% w/w, preferably from 12 to 60% w/w. In another aspect, when the dental appliance cleansing composition contains water as a solvent, the second sorbitan ester is present in an amount from 0.5 to 4% w/w, preferably from 1 to 2% w/w.

In one aspect, the present invention provides a dental appliance cleansing composition as defined in any previous aspect, wherein the second sorbitan ester is not itself another polyoxethylene sorbitan ester.

In one aspect, the present invention provides a dental appliance cleansing composition as defined in any previous aspect, which further comprises at least one solvent. Suitable solvents include water, propylene glycol, and a combination thereof.

In a further aspect, the dental appliance cleansing composition as defined in any previous aspect comprises at least one solvent in an amount from 0.2 to 95% w/w, preferably from 0.7 to 90% w/w.

In a further aspect, the dental appliance cleansing composition as defined in any previous aspect comprises propylene glycol in an amount from 0.2 to 15% w/w, preferably from 0.7 to 12% w/w In a further aspect, the dental appliance cleansing composition as defined in any previous aspect comprises water in an amount from 70 to 95% w/w, preferably from 80 to 95% w/w, more preferably from 85 to 90% w/w.

In one aspect, the present invention provides a dental appliance cleansing composition as defined in any previous aspect which further comprises at least one aroma or flavour oil. Suitable aroma or flavour oils for use in the instant invention include, but are not limited to, spearmint, menthol, peppermint, and mixtures thereof. In a further aspect, the dental appliance cleansing composition comprises at least one aroma or flavour oil selected from spearmint, peppermint, and mixtures thereof. In a further aspect, the dental appliance cleansing composition comprises spearmint oil and peppermint oil. In a further aspect, the dental appliance cleansing composition comprises at least one aroma or flavour oil in an amount from 0.1 to 2.0% w/w, preferably from 0.2 to 1.0% w/w.

In one aspect, the present invention provides a dental appliance cleansing composition as defined in any previous aspect which further comprises at least one preservative. In another aspect, the present invention provides a dental appliance cleansing composition as defined in any previous aspect which further comprises at least one preservative selected from potassium sorbate, sodium benzoate, phenoxyethanol, cetylpyridinium chloride, and combinations thereof. In a further aspect, the dental appliance cleansing composition comprises at least one preservative selected from potassium sorbate, phenoxyethanol, and combinations thereof, preferably a combination of potassium sorbate and phenoxyethanol. In a further aspect, the at least one preservative is present in an amount from 0.05 to 1.5% w/w, preferably from 0.1 to 1.0% w/w, more preferably from 0.25 to 0.75% w/w.

In one aspect, the present invention provides a dental appliance cleansing composition as defined in any previous aspect which further comprises a sweetener selected from sodium saccharin, aspartame, sucralose, and stevia; preferably sodium saccharin. The sweetener is present in an amount according to taste, for example 0.05% w/w.

In one aspect, the present invention provides a dental appliance cleansing composition as defined in any previous aspect which further comprises a pH adjuster such as citric acid, sodium hydroxide or sodium citrate, preferably citric acid. The dental appliance cleansing composition may further contain a sequestering agent such as disodium EDTA. In one aspect, the pH adjuster or sequestering agent are present at less than 1% w/w.

In one aspect, the present invention provides a dental appliance wipe impregnated with a cleansing composition as defined in any previous aspect.

In one aspect, the present invention provides a dental appliance wipe impregnated with a cleansing composition comprising:
a) a fatty acid isopropyl ester;
b) a polyoxyethylene sorbitan ester; and
c) a second sorbitan ester;
wherein the cleansing composition does not contain methanol, ethanol or isopropyl alcohol.

In another aspect, the present invention provides a dental appliance wipe impregnated with a cleansing composition comprising:
a) a fatty acid isopropyl ester;
b) a polyoxyethylene sorbitan ester; and
c) a second sorbitan ester;
wherein the cleansing composition does not contain alcohol.

In another aspect, the present invention provides a dental appliance wipe impregnated with a cleansing composition comprising:
a) a fatty acid isopropyl ester;
b) a polyoxyethylene sorbitan ester;
c) a second sorbitan ester; and
d) a solvent selected from propylene glycol, water, and a mixture thereof;
wherein the cleansing composition does not contain methanol, ethanol or isopropyl alcohol.

In one aspect, the invention provides a dental appliance wipe impregnated with a cleansing composition comprising:
a) a fatty acid isopropyl ester selected from isopropyl palmitate, isopropyl myristate, and combinations thereof;
b) a polyoxyethylene sorbitan ester selected from polysorbate 60 (TWEEN 60), polysorbate 65 (TWEEN 65), polysorbate 80 (also known as polyoxyethylene (20) sorbitan monooleate or TWEEN 80), polysorbate 81 (TWEEN 81), polysorbate 85 (TWEEN 85), and combinations thereof; and
c) a second sorbitan ester selected from sorbitan monostearate (also known as sorbitan stearate or SPAN 60), sorbitan monolaurate (SPAN 20), sorbitan palmitate (SPAN 40), and combinations thereof;
wherein the cleansing composition does not contain methanol, ethanol or isopropyl alcohol.

In one aspect, the invention provides a dental appliance wipe impregnated with a cleansing composition comprising:
a) a fatty acid isopropyl ester selected from isopropyl palmitate, isopropyl myristate, and combinations thereof;
b) a polyoxyethylene sorbitan ester selected from polysorbate 60 (TWEEN 60), polysorbate 65 (TWEEN 65), polysorbate 80 (also known as polyoxyethylene (20) sorbitan monooleate or TWEEN 80), polysorbate 81 (TWEEN 81), polysorbate 85 (TWEEN 85), and combinations thereof; and
c) a second sorbitan ester selected from sorbitan monostearate (also known as sorbitan stearate or SPAN 60), sorbitan monolaurate (SPAN 20), sorbitan palmitate (SPAN 40), and combinations thereof; and
d) a solvent selected from propylene glycol, water, and a mixture thereof;
wherein the cleansing composition does not contain methanol, ethanol or isopropyl alcohol.

In one aspect, the present invention provides a dental appliance wipe impregnated with a cleansing composition comprising:
a) isopropyl myristate;
b) polysorbate 80; and
c) sorbitan laurate;
wherein the cleansing composition does not contain methanol, ethanol or isopropyl alcohol.

In another aspect, the present invention provides a dental appliance wipe impregnated with a cleansing composition comprising:
a) isopropyl myristate;
b) polysorbate 80;
c) sorbitan laurate; and
d) a solvent selected from propylene glycol, water, and a mixture thereof;
wherein the cleansing composition does not contain methanol, ethanol or isopropyl alcohol.

In another aspect, the present invention provides a dental appliance wipe impregnated with a cleansing composition as defined in any previous aspect, wherein the cleansing composition does not contain alcohol e.g. is alcohol free.

DEFINITIONS

The terms "clean", "cleansing" or "cleaning" are used interchangeably herein to refer to the removal of food particles, stains, microbes/microorganisms, and other oral debris by the wiping and/or cleaning action, plus the breath freshening function of the inventive formulation.

The term "dental appliance", as used herein, refers to dentures or partial dentures, artificial teeth, removable orthodontic bridges and denture plates, both upper and lower types, orthodontic retainers and appliances, protective mouthguards, nightguards to prevent bruxism and/or Temporomandibular joint (TMJ) disorder, and the like.

The term "dental appliance cleanser", as used herein, refers to a formulation for use outside the mouth to clean dental appliances.

The term "microemulsion" as used herein, refers to a clear, thermodynamically stable, isotropic liquid mixture of oil and surfactant, in combination with a cosurfactant. The microemulsion may be free of water or in a diluted form. Once diluted, the microemulsion has uniform submicron size particles.

The term 'wipe' as used herein, refers to an insoluble substrate, including woven and non-woven substrates as well as sponges, for example cellulose substrate. Nonwoven substrates are preferred. By nonwoven is meant that the layer is comprised of fibres which are not woven into a fabric but rather are formed into a sheet or web structure, bonded together by entangling the fibre or filaments mechanically, thermally or chemically. The insoluble substrate is preferably a viscose polyester blend, a viscose polypropylene blend, or a viscose polyester polypropylene blend; more preferably a viscose polypropylene blend; more preferably still a 65% viscose-35% polypropylene blend. The insoluble substrate may be obtained from a wide variety of commercial sources. A preferred wipe according to the present invention is NOVONETTE™ Thermal Bond, a wipe available from Suominen. The insoluble substrate is not limited to any form, specific pattern, design or geometry. It may be plain, patterned or embossed and it can also be of any size or shape. The wipes of the present invention are preferably 11 cm×15 cm or 15 cm×20 cm. The insoluble substrate must not tear or snag and is intended to be disposed or discarded after a single use.

The term "wet wipes" as used herein, refers to the insoluble substrate in and on which a dental appliance cleansing composition according to the present invention is loaded. Once loaded, the wet wipe contains sufficient cleansing composition to make it wet, damp or moistened. That is the wipe has a loading factor of at least 2.0 grams of cleansing composition per gram of dry substrate.

The term 'fatty acid isopropyl ester' as used herein, refers to the ester of isopropanol and a suitable fatty acid such as myristic acid or palmitic acid. Isopropyl myristate is the ester of isopropanol and myristic acid (tetradecanoic acid), and is also known as propan-2-yl tetradecanoate, tetradecanoic acid 1-methylethyl ester or myristic acid isopropyl ester.

Isopropyl palmitate is the ester of isopropanol and palmitic acid (hexadecanoic acid) and is also known as propan-2-yl hexadecanoate, isopropyl hexadecanoate, hexadecanoic acid isopropyl ester, or hexadecanoic acid 1-methylethyl ester.

Examples of polyoxyethylene sorbitan esters according to the invention are selected from the group consisting of polysorbate 20 (TWEEN 20), polysorbate 21 (TWEEN 21), polysorbate 40 (TWEEN 40), polysorbate 60 (TWEEN 60), polysorbate 65 (TWEEN 65), polysorbate 80 (also known as polyoxyethylene (20) sorbitan monooleate or TWEEN 80), polysorbate 81 (TWEEN 81), polysorbate 85 (TWEEN 85), and combinations thereof; preferably polysorbate 60 (TWEEN 60), polysorbate 65 (TWEEN 65), polysorbate 80 (also known as polyoxyethylene (20) sorbitan monooleate or TWEEN 80), polysorbate 81 (TWEEN 81), polysorbate 85 (TWEEN 85), and combinations thereof;
more preferably polysorbate 80.

Examples of the second sorbitan esters according to the invention are selected from the group consisting of sorbitan monostearate (also known as sorbitan stearate or SPAN 60), sorbitan tristearate (SPAN 65), sorbitan monolaurate (SPAN 20), sorbitan palmitate (SPAN 40), sorbitan oleate (SPAN 80), sorbitan sesquioleate (SPAN 83), sorbitan trioleate (SPAN 85), sorbitan isostearate (SPAN 120), and combinations thereof;
preferably sorbitan monostearate (also known as sorbitan stearate or SPAN 60), sorbitan monolaurate (SPAN 20), sorbitan palmitate (SPAN 40), and combinations thereof;
more preferably sorbitan monolaurate (SPAN 20).

Preferably, the present invention provides a dental appliance cleansing composition or dental appliance wipe impregnated with a cleansing composition as defined in any previous aspect, wherein
b) the polyoxyethylene sorbitan ester is selected from polysorbate 60 (TWEEN 60), polysorbate 65 (TWEEN 65), polysorbate 80 (also known as polyoxyethylene (20) sorbitan monooleate or TWEEN 80), polysorbate 81 (TWEEN 81), polysorbate 85 (TWEEN 85), and combinations thereof; and c) the second sorbitan ester is selected from sorbitan monostearate (also known as sorbitan stearate or SPAN 60), sorbitan monolaurate (SPAN 20), sorbitan palmitate (SPAN 40), and combinations thereof;
OR
b) the polyoxyethylene sorbitan ester is selected from polysorbate 20 (TWEEN 20), polysorbate 21 (TWEEN 21), polysorbate 40 (TWEEN 40), and combinations thereof; and
c) the second sorbitan ester is selected from sorbitan oleate (SPAN 80), sorbitan sesquioleate (SPAN 83), sorbitan trioleate (SPAN 85), sorbitan isostearate (SPAN 120), and combinations thereof.

WIPES

The wet wipes according to the present invention are made by wetting the dry substrate with at least 1 gram of composition per gram of dry substrate. Preferably, the dry substrate is wetted with at least 2.0 grams, more preferably at least 3.0 grams and even more preferably at least 2.7 grams or 3.5 grams of composition per gram of the dry substrate.

The wipes according to the present invention may be individually packaged as single wipes, or as a multi-pack. Where the wipe is packaged as single wipes, each wipe may be packaged in an individual sachet with a number of such sachets being included in a box, for example 1, 14, 15, 20, 28, 30 or 40 sachets in a box. Where the wipe is packaged as a multi-pack, a number of wipes (for example 20, 25, 30, 40, 50 or 70) may be packaged within a re-sealable container, such as packs or containers which can be re-closed or sealed using adhesive labels or plastic lids.

The packaging enclosure for the wet wipes according to the present invention must protect the product from loss of flavour, and/or solvent. It must not interact with the product with resultant adverse effects on either the cleansing composition or package properties. The packaging for the wet wipes according to the present invention can be of any suitable form. Preferably, the packaging enclosure includes an aluminium barrier laminate and a hard-closable cap. The packaging may be of any suitable size and shape, preferably it should be small and easily portable.

EXPERIMENTAL

The following examples of compositions according to the present invention are intended as an illustration only and not a limitation on the scope of the invention. Various changes and modifications to the disclosed embodiments will be apparent to those skilled in the art and such changes and modifications may be made without departing from the spirit of the invention and the scope of the appended claims.

Method of Manufacture

The compositions according to the present invention may be prepared by admixing the ingredients in the appropriate relative amounts in any order that is convenient (see the Examples below). Preferably, the oil phase and aqueous phases are formed separately, and the two phases are then combined.

The wet wipes according to the present invention may be prepared by preparing a dry insoluble substrate of suitable size and then contacting the cleansing composition to said substrate by e.g. spray dispersion. Once prepared the wet wipes are transferred to an air tight resealable container of suitable size which is then sealed.

Examples 1 to 3 illustrate cleansing compositions of the invention which do not contain water.

| Ingredient | Example 1 % w/w | Example 2 % w/w | Example 3 % w/w |
|---|---|---|---|
| Isopropyl myristate | 60.90 | 34.50 | 13.63 |
| Sorbitan Laurate | 13.90 | 25.51 | 58.09 |
| Polysorbate 80 | 13.90 | 38.99 | 18.18 |
| Propylene Glycol | 10.30 | — | 9.10 |
| Peppermint/Spearmint Oil | 1.00 | 1.00 | 1.00 |
| Total | 100.00 | 100.00 | 100.00 |

Examples 4 to 8 illustrate cleansing compositions of the invention which contain propylene glycol and water.

| Ingredient | Example 4 % w/w | Example 5 % w/w | Example 6 % w/w | Example 7 % w/w | Example 8 % w/w |
|---|---|---|---|---|---|
| Purified Water | 74.43 | 94.33 | 89.35 | 89.34 | 88.87 |
| Isopropyl myristate | 14.98 | 3.00 | 6.09 | 5.89 | 5.89 |
| Sorbitan Laurate | 3.48 | 0.70 | 1.39 | 1.39 | 1.39 |
| Polysorbate 80 | 3.48 | 0.70 | 1.39 | 1.39 | 1.39 |
| Propylene Glycol | 2.58 | 0.52 | 1.03 | 1.03 | 1.03 |
| Cetylpyridinium Chloride | 0.05 | 0.05 | 0.05 | 0.05 | — |
| Potassium Sorbate | — | — | — | 0.50 | 0.40 |
| Phenoxyethanol | — | — | — | — | 0.30 |
| Sodium Benzoate | 0.50 | 0.50 | 0.50 | — | — |
| Citric Acid | — | — | — | 0.06 | 0.28 |
| Peppermint/Spearmint Oil | 0.50 | 0.20 | 0.20 | 0.30 | 0.30 |
| Disodium EDTA | — | — | — | — | 0.10 |
| Saccharin Sodium | — | — | — | 0.05 | 0.05 |
| Total | 100.00 | 100.00 | 100.00 | 100.00 | 100.00 |

Reference Example A

| Ingredient | % w/w |
|---|---|
| Purified Water | 88.30 |
| Glycerol | 10.00 |
| Cremophor RH60 ™ (PEG-60 hydrogenated castor oil) | 0.70 |
| Sodium Citrate | 0.50 |
| Peppermint Oil | 0.20 |
| Zinc Chloride | 0.10 |
| Cetylpyridinium Chloride | 0.05 |
| Methylparaben | 0.05 |
| Propylparaben | 0.05 |
| Saccharin Sodium | 0.05 |
| Total | 100.00 |

Reference Example A is a representative alcohol-free mouthwash formulation.

TEST DATA

Biofilm development on acrylic surfaces of dentures most frequently occurs following poor compliance with denture-cleansing regimes. The colonising biofilm cells and particularly those of the fungal genus *Candida* are thought to be the main causes of *Candida*-associated denture stomatitis. This infection is prevalent occurring in >65% of denture wearers. Clinical presentation is seen as areas of erythema of the palate in contact with the fitting surface of the denture.

Clearly, good compliance with an appropriate denture cleansing regime is key to protecting against *Candida*-associated denture stomatitis. Generally, such a cleansing protocol involves the soaking of the denture in an appropriate cleanser. Additionally, denture surfaces can be brushed using a toothbrush coupled with proprietary toothpastes or gels.

The aim of this study was to use an in vitro approach to evaluate the efficiency of dental wipes impregnated with the compositions of Example 6 and Example 8 on the removal of microorganisms from denture base acrylics.

Materials & Methods

Development of Microbial Biofilms on Acrylic Surfaces

Squares (1 $cm^2$) of denture acrylic previously pre-conditioned by immersion in sterile artificial saliva for 24 h at 37° C. were immersed in a prepared and standardised microbial inoculum for 72 h at 37° C. After incubation, the contaminated acrylic was immersed in sterile water for 5 min to remove loosely attached/planktonic microorganisms.

Microbial Removal Using a Cleansing Wipe

To perform a standardised 'wiping' procedure, a cleansing wipe was attached to the surface of a dental material polishing instrument. This apparatus had a rotating turntable that enabled operation at speeds of between 50-600 rev/min. The diameter of the turntable was 300 mm and was therefore ideally suited for large or small specimens. In this study, a cleansing wipe was positioned on the surface of the rotating turntable so that it rotated with the motion of the turntable. A static arm incorporating a pressure weight was mounted above the turntable, and held the acrylic squares in a fixed position and in direct contact with the cleansing wipe. Varying degrees of wiping were achieved by maintaining a constant rotation and changing the time. In these investigations, the ability of cleansing wipes to remove microbial colonisation by wiping at 100 rev/min for 60 s and/or 100 rev/min for 10 s or a warm water rinse under a standardised flow were assessed. Controls were of acrylic surface that had not been exposed to the wiping process.

After wiping, the microorganisms on the surface of the acrylic were fixed in 4% (v/v) formalin for 24 h. Propidium iodide stained images from each test group were examined by confocal laser scanning microscopy (CLSM). Images were converted to binary black and white to determine percentage coverage using ImageJ software (Rasband, W. S., ImageJ, U.S. National Institutes of Health, Bethesda, Md., USA, http://imagej.nih.gov/ij/, 1997-2014). Quantitative data analysis was undertaken using SPSS Statistics (v20) (IBM). Multiple analyses were performed using Kruskal-Wallis test and the Mann-Whitney-Wilcoxon test to compare the area of colonisation between the pairs of treatment groups. Significant differences were determined at the 0.05 level.

Two studies were performed using different treatments.

Study 1

Samples of the following were assessed:
1. Non-wiped
2. Reference Example A wiped for 10 s
3. Reference Example A wiped for 60 s
4. Example 6 wiped for 10 s
5. Example 6 wiped for 60 s Results Quantitative results of acrylic colonisation, determined for 15 fields of view (5 from each of three replicate acrylic specimens) are presented in Table 1.

TABLE 1

Percentage area of acrylic colonised by microorganisms post application of a cleansing wipe

| | Percentage area colonised by microorganisms Treatment method | | | | |
|---|---|---|---|---|---|
| | Non wiped | 10 s wiped Reference Example A | 60 s wiped Reference Example A | 10 s wiped Example 6 | 60 s wiped Example 6 |
| Mean | 2.1140 | 1.1259 | 0.4247 | 0.6302 | 0.1569 |
| Standard Dev. | 2.63586 | 1.34142 | 0.49956 | 0.81542 | 0.15109 |
| Median | 0.9636 | 0.9298 | 0.1415 | 0.2609 | 0.0847 |

A Shapiro-Wilk Test showed that the data was not normally distributed (P<0.0001). ANOVA revealed that there was a significant difference in the levels of colonisation between the test groups (P=0.02). Using the Tukey post-hoc test on the one-way ANOVA showed that compared with the non-wiped control, significant reduction in residual colonisation occurred with Comparative Example A wiping for 60 s (P=0.012), Example 6 wiping for 10 s (P=0.037) and Example 6 wiping for 60 s (P=0.002). There was no significant reduction evident between non-wiped controls and wiping with Reference Example A for 10 s (P=0.304).

Conclusions

It was apparent that wiping the denture acrylic surface with both Comparative Example A and Example 6 wipes for 60 s enabled significant removal of microorganisms compared with non-wiped controls. In addition, significant reduction in microbial removal was also determined using the Example 6 wipe for 10 s.

This removal study shows that the physical action of wiping the denture acrylic for 10 seconds with a wipe impregnated with a composition according to the present invention provides improved removal when compared with a wipe impregnated with a representative mouthwash solution.

Study 2

Samples of the following were assessed:
1. Non-wiped
2. Water rinse for 10 s
3. Example 8 wiped for 10 s Results Quantitative results of acrylic colonisation, determined for 150 fields of view (5 from each of 30 replicate acrylic specimens) are presented in Table 2.

TABLE 2

Percentage area of acrylic colonised by microorganisms post a water rinse or application of a cleansing wipe

| | Percentage area colonised by microorganisms Treatment method | | |
|---|---|---|---|
| | Non wiped | 10 s Water Rinse | 10 s wiped Example 8 |
| Mean | 0.3478 | 0.2331 | 0.1843 |
| Standard Dev. | 0.59722 | 0.16908 | 0.13716 |
| Median | 0.2313 | 0.1882 | 0.1526 |

A Shapiro-Wilk Test showed that the data was not normally distributed (P<0.0001). Independent-samples Kruskal-Wallis showed that there was significant difference in colonisation between test groups (P<0.0001). Mann-Whitney-Wilcoxon testing to compare non-wiped controls with cleaned samples revealed significant reduction in residual colonisation with Example 8 wiping for 10 s (P<0.0001), and washing with flowing water for 10 s (P=0.018). A significant reduction in colonisation was also evident for the wiped samples compared with water washed samples (P=0.013).

Conclusions

This study has revealed that 10 s wiping of a microbial-contaminated acrylic using Example 8 resulted in a significant removal of microorganisms compared with both non-wiped controls and water rinsed samples.

The invention claimed is:

1. A dental appliance cleansing composition comprising:
   a. a fatty acid isopropyl ester;
   b. a polyoxyethylene sorbitan ester; and
   c. a second sorbitan ester;
   wherein the cleansing composition comprises 0.7 to 12% w/w of propylene glycol and 85 to 90% w/w of water and does not contain methanol, ethanol or isopropyl alcohol, wherein the cleansing composition is in the form of a microemulsion.
2. A dental appliance cleansing composition according to claim 1, wherein the fatty acid ester isopropyl ester is selected from isopropyl palmitate, isopropyl myristate, and combinations thereof.

3. A dental appliance cleansing composition according to claim 1, wherein the polyoxyethylene sorbitan ester is selected from polysorbate 20, polysorbate 21, polysorbate 40, polysorbate 60, polysorbate 65, polysorbate 80, polysorbate 81, polysorbate 85, and combinations thereof.

4. A dental appliance cleansing composition according to claim 1, wherein the second sorbitan ester is selected from sorbitan monostearate, sorbitan tristearate, sorbitan monolaurate, sorbitan palmitate, sorbitan oleate, sorbitan sesquioleate, sorbitan trioleate, sorbitan isostearate, and combinations thereof.

5. A dental appliance cleansing composition according to claim 1 wherein the fatty acid isopropyl is present in an amount from 3 to 15% w/w.

6. A dental appliance cleansing composition according claim 1, wherein the polyoxyethylene sorbitan ester is present in an amount from 0.5 to 4% w/w.

7. A dental appliance cleansing composition according claim 1, wherein the second sorbitan ester is present in an amount from 0.5 to 4% w/w.

8. A dental appliance cleansing composition according to claim 1, wherein the composition further comprises at least one preservative selected from potassium sorbate, sodium benzoate, phenoxyethanol, cetylpyridinium chloride, and combinations thereof.

9. A dental appliance cleansing wipe impregnated with a composition as defined in claim 1.

* * * * *